United States Patent [19]

Barland

[11] 4,022,056
[45] May 10, 1977

[54] HARDNESS TESTING APPARATUS

[76] Inventor: Lauri C. Barland, Box 265, West Chester, Pa. 19380

[22] Filed: Dec. 12, 1975

[21] Appl. No.: 640,289

[52] U.S. Cl. .................................................. 73/78
[51] Int. Cl.² ......................... G01N 3/08; G01N 3/40
[58] Field of Search ............................ 73/78, 90, 94

[56] References Cited

UNITED STATES PATENTS

| 534,994 | 3/1895 | Buzby | 73/90 |
|---|---|---|---|
| 2,228,902 | 1/1941 | Allen | 73/78 |
| 2,703,492 | 3/1955 | Brissette et al. | 73/94 |
| 2,975,630 | 3/1961 | Michel | 73/94 |

*Primary Examiner*—James J. Gill
*Assistant Examiner*—Anthony V. Ciarlante
*Attorney, Agent, or Firm*—Paul & Paul

[57] ABSTRACT

Hardness testing apparatus is provided having a pair of anvil elements adapted to receive and hold a test object which may then be subjected to increasing pressures by application of an increasing force to one of the anvil elements while holding the other anvil in a fixed position. The increasing force is applied through a pivotally mounted element, one end of which operatively engages the anvil and which is provided with a weight which is movable toward its other end. Drive means for moving the weight along the pivotally mounted element are provided as well as means for stopping such movement and indicating the applied force when the test object fractures. Means are also provided for reversing the direction of motion of the weight at the time of fracture of the test object and to return the weight to a position where it is in equilibrium with the anvil.

16 Claims, 7 Drawing Figures

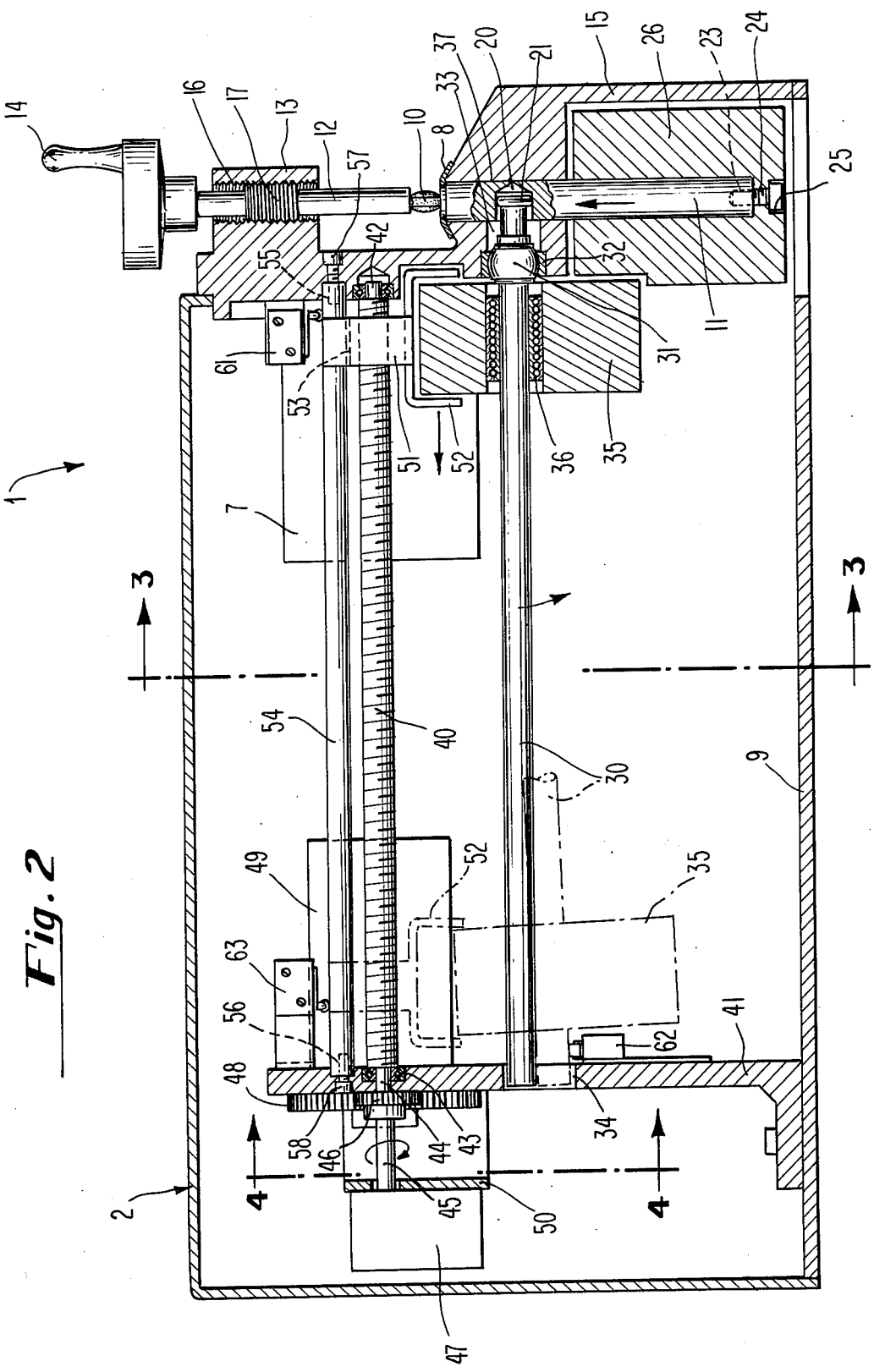

HARDNESS TESTING APPARATUS

BACKGROUND OF THE INVENTION

In the manufacturing and processing of pharmaceutical tablets and the like, it is usually necessary to test such tablets for hardness. Such tests in the past have been carried out in apparatus utilizing springs or compressed air or, in some cases, an indicator is mechanically actuated in response to movement of a mechanical linkage having the test tablet interposed as one element in the linkage.

Problems inherent in these models include interference caused by tablet particles, calibration difficulties and inherent difficulties of reproducibility of test results.

THE PRESENT INVENTION

The present invention is directed to providing an apparatus for testing the hardness of pharmaceutical tablets and the like, utilizing a pivotal element provided with a movable weight for applying a continuously increasing pressure to a tablet being tested, the pressure increasing as a function of the movement of the weight along the pivotal element.

The tablet to be tested by the apparatus of the present invention is held between upper and lower anvil means, the upper anvil being vertically adjustable to accommodate various sizes of pharmaceutical tablets and also being mounted in a way to resist pressure applied to the tablet through the lower anvil. In the particular preferred embodiment of the invention illustrated in the drawings, the pivotal means comprises a rod provided with a journal which is mounted in a bearing. The movable weight is initially positioned on the rod at a predetermined short distance from the pivot point of the rod. The end of the rod on the side of the pivot opposite to the weight engages a vertically movable anvil element which is affixed to a movable counterweight at one end which provides a lower anvil surface at the other end. In this initial position the movable weight and the counterweight with its anvil are of predetermined weights such that they are substantially in equilibrium and, therefore, there is substantially zero pressure applied to the tablet by the pivotal rod at this time.

In the preferred embodiment, means are provided for continuously moving the movable weight along the pivotal rod away from the pivot point. This is accomplished by means of a yoke which engages the movable weight and which in turn is caused to move through the action of a threaded drive screw. The yoke engages a guide rod at its upper end and is thereby guided and maintained in a vertical position. It will thus be seen that displacement of the movable weight along the pivotal rod as the weight is displaced from the equilibrium point results in a continuously increasing force acting upwardly at the position where the end of the pivotal rod engages the lower anvil rod. Normally at some point in the travel of the movable weight along the pivotal rod, the force applied to the tablet through the lower anvil is just sufficient to fracture the tablet. At this point there will be a sudden removal of resistance to upward motion of the lower anvil and the pivotal rod will move upwards at this end and will move downwardly at the opposite end. This sudden downward movement of this end of the pivotal element is used to actuate a switch which operates to reverse the direction of rotation of the threaded drive screw in order to return the movable weight to the equilibrium position.

The threaded drive screw is driven by a constant speed reversible motor connected to the drive screw by means of suitable gearing consisting of a drive gear and a driven gear. The drive gear is fixedly attached to the shaft of the threaded drive screw to which there is also attached the shaft of an encoder which provides a predetermined number of pulses per revolution of the drive screw shaft. These encoder pulses are used to activate a counter display. Additional limit switches are provided which are actuated by the yoke guide member to reverse the motor at a predetermined limit of travel of the movable weight away from the pivot point in the event the test object does not fracture and to deactivate the motor when the movable weight returns to its equilibrium position.

Accordingly, it is a primary object of this invention to provide a novel testing apparatus and method for testing the hardness of pharmaceutical tablets and the like which produces consistent results from test to test.

It is another object of this invention to provide an inexpensive and direct and, therefore, expedient means to generate and display accurate hardness or fracture pressure data with a minimum of calibration problems.

Other objects and advantages will be readily apparent to those skilled in the art from the reading of the following brief descriptions of the drawings, figures, detailed descriptions of the preferred embodiments and the appended claims.

IN THE DRAWINGS

FIG. 2 is an enlarged sectional view taken generally along the lines 2—2 of FIG. 1 wherein the internal structure of the hardness testing apparatus is illustrated.

DESCRIPTION OF THE PREFERRED EMBODIMENTS

Figure 1:
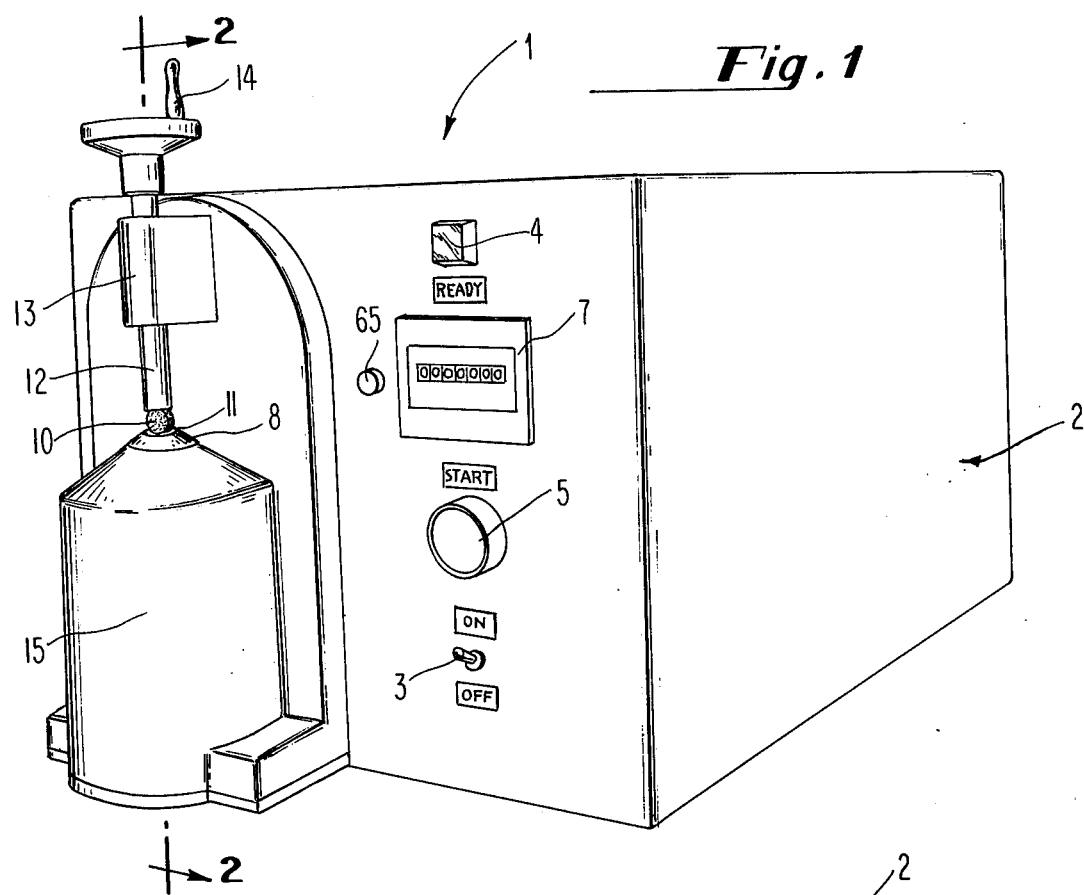
FIG. 1 is a front perspective view of the hardness testing apparatus of the present invention.

Referring now to the drawings in detail, reference is first made to FIG. 1, wherein the apparatus 1 is generally illustrated as comprising a casing 2 with a front wall having an off/on toggle switch 3 for energizing the electronic circuitry of the apparatus, a pilot light 4 which indicates the circuitry has been energized and is ready for use, a start push button 5 which when depressed starts a motor which activates the drive means more fully discussed hereinafter and which activates a counter 7 which gives a direct read-out to visually indicate the pressure at which the tablet fractures.

A pharmaceutical tablet 10 is held between lower anvil 11 and upper anvil 12. Upper anvil 12 is adjustably mounted in upper anvil housing 13, both upper anvil 12 and upper anvil housing 13 being threaded at 17 and 16 respectively (as shown in FIG. 2) to provide vertical adjustment of anvil 12 to accommodate various sizes of test objects by operation of rotatable handle 14 which is attached to anvil 12. Lower anvil 11 is used for applying pressure to the tablet 10. Upper anvil 12 provides a fixed resistance to this pressure. Attached to lower anvil 11 at its upper end is a circular, downwardly sloping shield 8 which is provided with a central opening into which the end of anvil 12 is fitted. Shield 8 prevents tablet particles from entering the bore 37 within which rod 11 is guided.

Lower anvil 11 is provided with a cavity 20 which accepts the end of pivotal rod 30 with contact being made by enlarged surface 21. Counterweight 26 is attached to anvil 11 by means of threaded bolt 24 which engages threads 23 formed at the lower end of rod 11. The head of bolt 24 is seated in cavity 25 formed in the lower part of counterweight 26.

Pivotal rod 30 is mounted in anvil housing 15 by means of journal 31 mounted in bearing 32 which is seated in anvil housing 15. Weight 35 is movably mounted on pivotal rod 30 by means of ball bushing 36 which enables weight 35 to move relative to pivotal rod 30. In the preferred embodiment, weight 35 is machined to 2 kilograms and applies a constantly increasing force to lower anvil 11 through spherical surface 21 as weight 35 is moved leftward on pivotal rod 30. When weight 35 is at the position illustrated in FIG. 2, weight 35 acting through pivotal rod 30 at spherical radius 21 is in equilibrium with lower anvil means 11 and associated counterweight 26.

In the preferred embodiment, weight 35 is moved laterally on rod 30 by rotation of a threaded drive screw 40 which is supported at its rightmost end in anvil casing 15 in bearing 42 and at its leftmost end by bearing 43 mounted in back plate 41 which is bolted to base plate 9. The leftmost end of threaded drive screw 40 has a shaft extension 44 of a radius less than threaded drive screw 40. Drive gear 46 is attached to shaft extension 44 which extends through gear 46 and is attached to the shaft of converter 47 by means of a hollow sleeve 45. Driven gear 48 is attached to the drive shaft of a reversible motor 49 and engages drive gear 46 as shown in FIG. 2. Converter 47 is preferably a reed type encoder Model 111 marketed by Disc Instruments, Inc. of Costa Mesa, Calif. The pulsed output of encoder 47, which in the preferred form is 20 pulses per revolution, is fed to counter 7 which preferably is Event Counter Model 55-4 marketed by Vorne Industries, Inc., 5023 W. Belmont Ave., Chicago, Ill. This event counter has an LED seven segment display which is solid state activated.

Threaded drive screw 40 engages yoke block 51 which is also threaded (not shown). In the preferred embodiment drive screw 40 has ten threads to the inch. On rotation of drive screw 40, yoke block 51 moves weight 35 through movement of arms 52 along pivotal rod 30 in either direction depending upon the direction of rotation of drive screw 40. The downward pivoting of weight 35 and pivotal rod 30 is not obstructed even when weight means 35 is in its leftwardmost position as illustrated by the dotted lines in FIG. 2. The yoke block arms 52 allow weight 35 to freely move yet are sufficiently structured to enable engagement of weight 35, even in its leftwardmost position, to move weight 35 rightwardly along pivotal rod 30 to the starting position.

Figure 3:
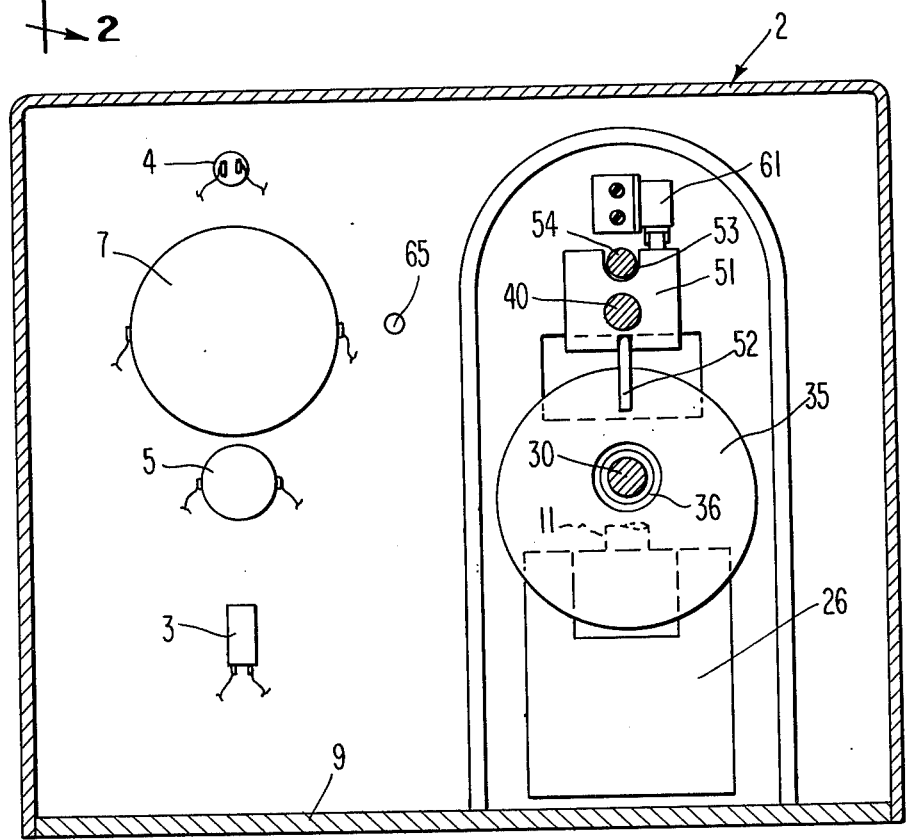
FIG. 3 is a sectional view taken generally along the lines 3—3 of FIG. 2.
Figure 4:
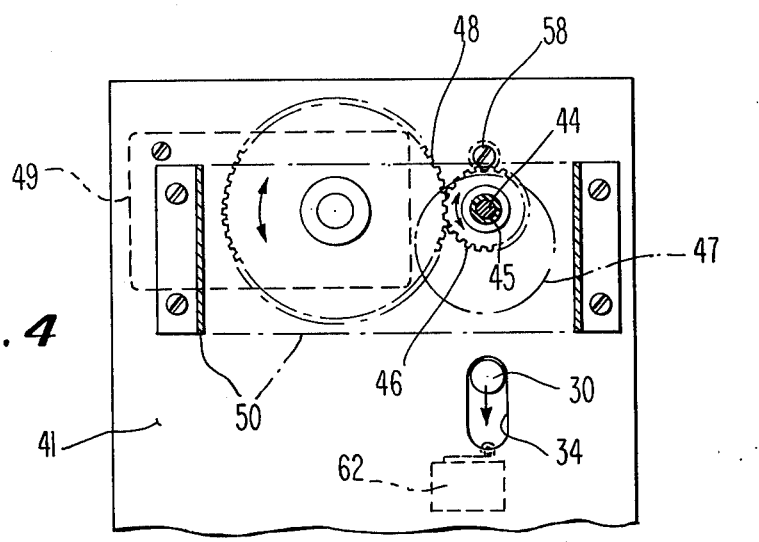
FIG. 4 is a sectional view taken generally along the lines 4—4 of FIG. 2.

Also, in the preferred embodiment, yoke block 51 is slotted at 53 (best seen in FIG. 3) so that when yoke block 51 moves from the rightward end of threaded drive screw 40 leftwardly, it is guided and maintained in a vertical position by rod 54 which is mounted in anvil housing 15 by bolt 57 engaging threads 55 and in plate 41 by bolt 58 engaging threads 56.

Microswitches 61 and 63 are operated by the upper end of yoke 51 as it is moved relative to guide rod 54. Microswitch 62 is operated when pivotal rod 30 moves up or down during operation of the apparatus. The effects produced by operation of the apparatus are set forth in the description of the electronic circuit of FIG. 5 and in the explanation of its operation as hereinafter set forth.

Figure 5:
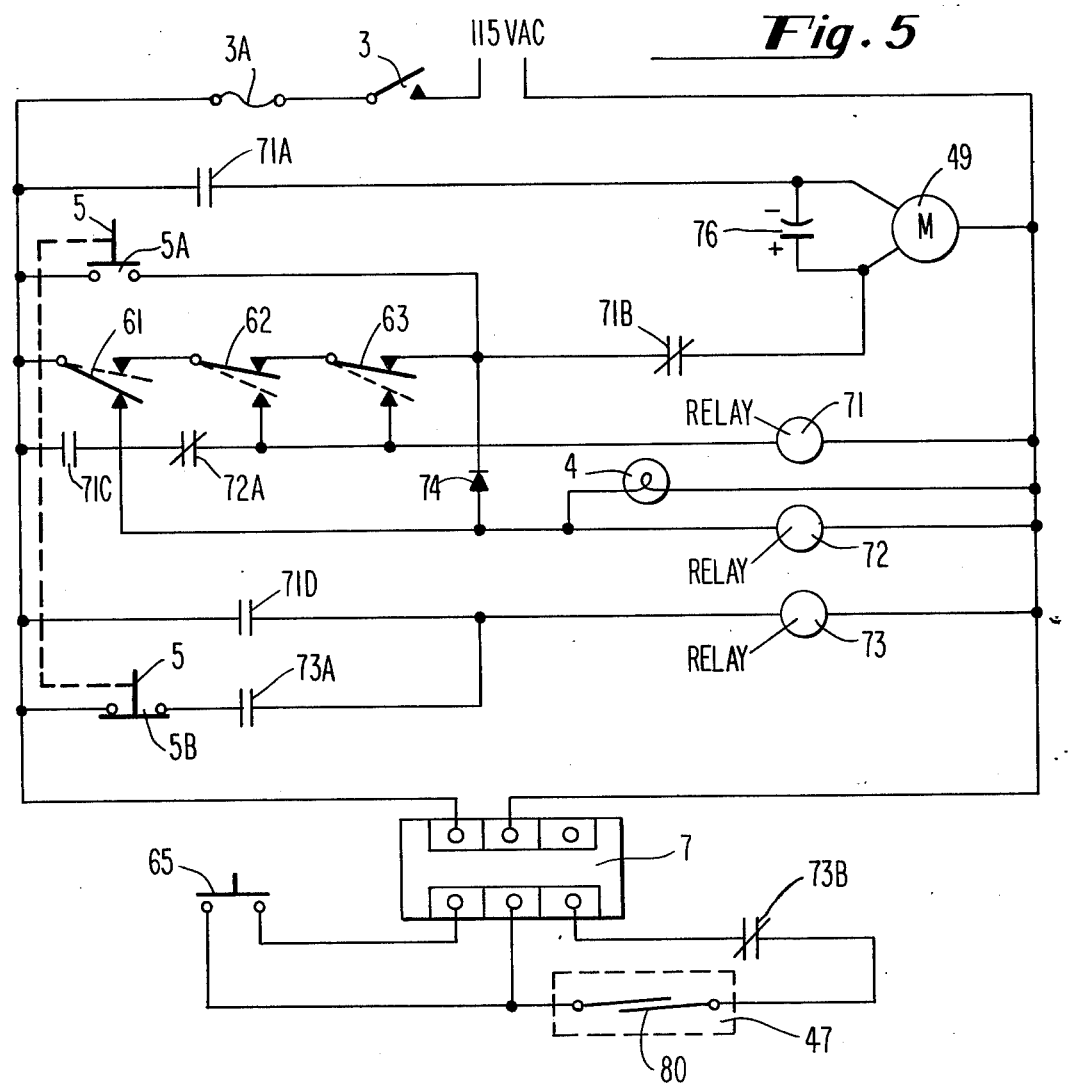
FIG. 5 is a schematic drawing illustrating the electronic control system of the present invention.

In FIG. 5 there is shown a circuit diagram in which the various electronic components of the apparatus and their interconnections are shown. In FIG. 5 an OFF/ON switch is shown at 3 between one side of the power line and fuse 3A. Also shown is reversible electric motor 49 and its associated capacitor 76, three microswitches 61, 62 and 63 and three relay solenoids 71, 72 and 73. Capacitor 76 is preferably about 4 MFD rated at 370 Volts AC. The contact points for the relay of solenoid 71 are shown at 71A, 71B, 71C and 71D. Similarly, the contact points associated with solenoid 72 are shown at 72A and the contact points associated with solenoid 73 are shown at 73A and 73B. All of said contact points which are normally open are shown open and those which are normally closed have a diagonal line passing through them. Encoder 47 is designated by a dashed line rectangle containing reed switch 80 which makes and breaks contact as the encoder shaft rotates. The pulsed output thus generated by encoder 47 is shown connected to counter 7 through normally closed contacts 73B. The remaining elements of FIG. 5 consist of push button switch 5 which has normally open contacts 5A and normally closed contacts 5B, a reset push button switch 65 and a ready light 4.

The operation of the circuit shown in FIG. 5 is as follows. With toggle switch 3 in the closed position, solenoid 72 is energized through microswitch 61 which is closed when weight 35 is in its equilibrium position. Ready light 4 is also energized at this time. With solenoid 72 energized, contact points 72A are opened which has the effect of deenergizing solenoid 71 which otherwise would be held in energized condition after one test cycle through its closed contacts 71C.

With a tablet held in the test position shown in FIG. 2, the apparatus is in condition for starting a hardness test. This is initiated by momentarily depressing push button switch 5 which has the effect of closing contacts 5A and opening contacts 5B, thus energizing motor 49 and connecting encoder 47 to counter 7. Motor 49 starts weight 35 in motion along rod 30 away from its equilibrium position. This immediately results in microswitch 61 moving to the dotted line position whereupon solenoid 72 is deenergized which results in its contact points 72A reverting to their normally closed position. Motor 49 will continue to run since it is energized through microswitches 61, 62, 63 and normally closed contacts 71B. This condition continues until microswitch 62 is thrown to the dotted line position as a result of pivotal rod 30 dropping in response to fracture of the tablet or until microswitch 63 is thrown to the dotted line position by travel of weight 35 to its limit position. On either one of these events solenoid 71 will be energized and its contacts 71C will close, thus holding solenoid 71 energized. At the same time contacts 71B will open and contacts 71A will close through energization of solenoid 71. This will cause motor 49 to reverse and this will reverse the direction of rotation of drive screw 40 and cause weight 35 to return to its equilibrium position whereupon microswitch 61 will be thrown to its solid line position. This will energize solenoid 72 and thus cause its contacts 72A to open thereby deenergizing solenoid 71 which in turn will open contacts 71A and thus deenergize motor 49. The circuit will then have returned to the ready position and this condition will be indicated by the fact that ready light 4 will be on.

The remaining solenoid 73 is provided to stop and hold the count read-out at counter 7 whenever solenoid 71 is energized. This is accomplished through closing contacts 71D when solenoid 71 is energized, thus energizing solenoid 73. This causes contacts 73B to open thereby disengaging counter 7 from the output of encoder 47. Contacts 73A are closed when solenoid 73 is energized, thus holding solenoid 73 energized whether or not contacts 71D are closed. However, when the circuit is in its start condition, solenoid 73 is deenergized on actuating start button 5 since contacts 5B open at that time. This results in deenergizing solenoid 73 and in opening contacts 73A and in returning contacts 73B to their normally closed position, thus reconnecting the output of encoder 47 to counter 7. Push button switch 65 is provided for resetting counter 7 to zero.

Diode 74, rated at 400 volts and 1 amperes, is provided to apply a holding current to the winding of motor 49 when microswitch 61 goes to the position shown in FIG. 5 at a time when contacts 71B are in their normally closed position. This configuration occurs when weight 35 is in a position where yoke 51 contacts microswitch 61. The dynamic braking of motor 49 which results from impressing the half wave current passing through diode 74 on the winding of motor 49 effectively prevents continued travel of yoke 51 beyond contact with microswitch 61 when yoke 51 is returned to its starting position. This has the effect of preventing yoke 51 from moving beyond contact with microswitch 61 through inertia. It is desirable to prevent such inertial travel in order to eliminate what otherwise would be a danger of a locked condition between the threads of yoke 51 and the threads of drive screw 40 at the far end thereof. Likewise, the dynamic braking action gives a positive positioning of yoke 51 at the starting position after it has been returned.

Figure 6:
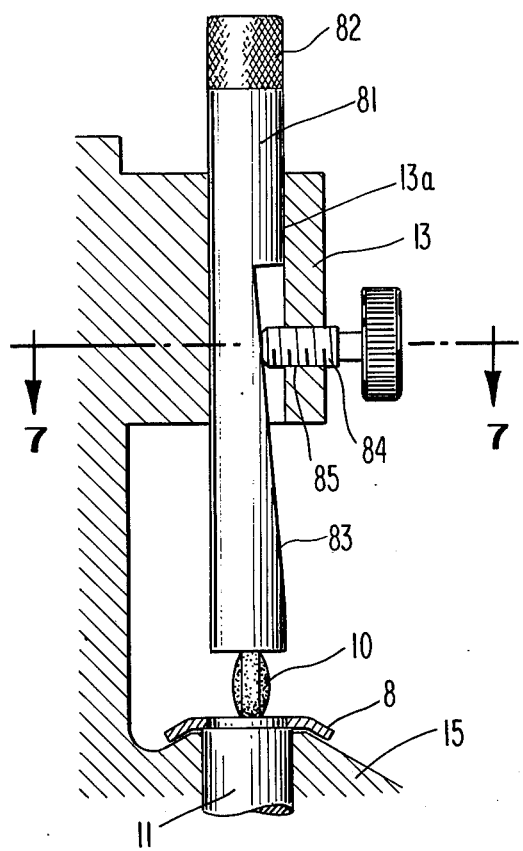
FIG. 6 is an enlarged fragmentary view of an alternative embodiment.
Figure 7:
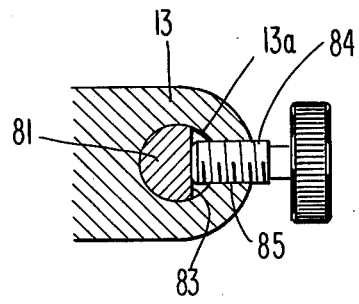
FIG. 7 is a sectional view taken along the lines 7—7 of FIG. 6.

FIG. 6 is an enlarged fragmentary view partly in section of an alternative embodiment of the head and anvil elements of the present invention. This alternative embodiment which is also shown in cross section in FIG. 7 is provided for use of the present invention in making hardness measurements where one of the requirements is to make repeated measurements of the hardness of tablets in rapid sequence.

As shown in FIG. 6, upper anvil housing 13 is provided with a bore 13a which is adapted to receive upper anvil 81 which fits within the bore 13a in sliding engagement. Anvil 81 is provided with a knurled circumferential surface 82 in order to give a gripping surface for manual vertical movement of anvil 81 within bore 13a. Anvil 81 has an inclined surface 83 formed by cutting out a part of anvil 81 in such a way as to provide a flat surface 83 inclined inwardly at an angle of about 5°. Threaded set screw 84 is mounted in tapped hole 85 and is adapted to engage flat surface 83 in order to hold anvil 81 in position after it has been adjusted to be in proper contact with tablet 10. The slope of surface 83 provides an effective resistance to the upward force which is transmitted to anvil 81 through the force applied to anvil 11.

Having thus described and illustrated my invention by reference to a preferred embodiment thereof, I claim:

1. A hardness testing apparatus for testing the hardness of tablets by measuring the compressive force required to fracture the same comprising spaced apart upper and lower anvils, said lower anvil for applying an upward force to said tablet, said upper anvil being vertically adjustable to hold said tablet against said lower anvil and means for securing said upper anvil in fixed position to resist said compressive force when applied by said lower anvil, lever means for applying an increasing upward force to said lower anvil, said lever means comprising a pivotally mounted element in operative engagement with said lower anvil, a weight mounted on said pivotally mounted element and laterally movable relative thereto, drive means for moving said weight laterally, and display means operatively connected to said drive means for indicating the force applied to said tablet as a function of the movement of said drive means, control means for operating said drive means and means for holding said display on fracture of said tablet.

2. Apparatus of claim 1, wherein said drive means includes a threaded rotatable drive screw, a threaded yoke block operatively engaging said drive screw and positioned to operatively engage said weight, and a reversible motor operatively engaging said drive screw whereby said motor and drive screw provide lateral movement of said yoke and said weight.

3. Apparatus of claim 2, wherein said yoke block further contains a slotted portion and yoke block arms positioned to engage said weight, guide means operating in conjunction with said slotted portion for maintaining said yoke in a substantially vertical position during lateral movement thereof, said weight being free to move vertically in said yoke arms when said lever means pivots.

4. Apparatus of claim 3, further including a lower anvil housing provided with a bore to receive said lower anvil and containing an opening to receive said lever means, a journal bearing mounted in said lower anvil housing for receiving said pivotally mounted element whereby an accurate measurement of said fracture force is indicated by said display means as a result of the precise and unimpeded movement of said weight and said pivotally mounted element about said journal bearing.

5. Apparatus of claim 2, wherein said display means further includes an encoder connected to said drive screw for providing a predetermined number of pulses per revolution of said drive screw and a counter operatively connected to said encoder into which said pulses are fed.

6. Apparatus of claim 1 wherein said control means includes means for reversing said drive means whereby the direction of motion of said weight is reversed.

7. Apparatus of claim 6 wherein said control means further includes means for deactivating the drive means when the weight reaches a predetermined position in response to the reversed motion.

8. Apparatus of claim 7 wherein said control means further includes means for impressing a dynamic braking current on said drive means when the weight reaches a predetermined position in response to the reversed motion.

9. Apparatus of claim 1 wherein said control means includes means for reversing said drive means on fracture of the test object in response to movement of said lever means.

10. Apparatus of claim 9, wherein said means for holding said display on fracture of said tablet maintains said display when the direction of motion of said drive means is reversed.

11. Apparatus of claim 1, wherein said upper anvil is threaded, and wherein said means for securing said upper anvil in fixed position to resist said compressive force includes an upper anvil housing, said housing being provided with a threaded bore for receiving said threaded upper anvil, and a rotatable handle attached to said upper anvil whereby the rotation of said handle permits vertical adjustment of said threaded upper anvil.

12. Apparatus of claim 1, wherein said means for securing said upper anvil in fixed position to resist said compressive force includes a threaded set screw, an upper anvil housing provided with a bore to receive said upper anvil in sliding engagement and containing a tapped hole for receiving said threaded set screw, said upper anvil further provided with knurled circumferential surface for manually gripping said anvil and vertically moving said anvil within said bore, said anvil having an inwardly inclined flat surface whereby said threaded set screw is adjusted to engage said flat surface to hold the upper anvil in position after said anvil is adjusted to be in proper contact with said tablet.

13. Apparatus of claim 1, further including a lower anvil housing provided with a bore to receive said lower anvil and containing an opening to receive said pivotally mounted element.

14. Apparatus of claim 13, wherein said lower anvil contains a reception means for engaging said lever means, said lever means further including a journal bearing mounted in said lower anvil housing for receiving said pivotally mounted element, said pivotally mounted element having a far end and a near end with respect to said journal bearing, said near end having an enlarged surface operatively engaging said reception means of said lower anvil, said journal bearing engaging said pivotally mounted element slightly inward of said enlarged surface, said weight engaging said pivotally mounted element at a position near said journal bearing, said position of said weight being at the furthest point of its travel away from said far end, whereby said upward increasing force transmitted to said lower anvil is approximately zero at such position, the total weight of said lower anvil substantially equaling that of said weight acting through said pivotally mounted element.

15. Apparatus of claim 14, further including a counterweight attached to said lower anvil, whereby the weight of said lower anvil and said counterweight is substantially equal to that of said weight acting through said pivotally mounted element.

16. Apparatus of claim 13, further including a shield attached to said lower anvil for supporting said tablets and preventing them for entering said lower housing through said bore upon the fracture of said tablet.

* * * * *